(12) United States Patent
Graham

(10) Patent No.: US 9,414,869 B2
(45) Date of Patent: Aug. 16, 2016

(54) BONE FIXATION ASSEMBLY

(71) Applicant: THE CLEVELAND CLINIC FOUNDATION, Cleveland, OH (US)

(72) Inventor: Thomas J. Graham, Novelty, OH (US)

(73) Assignee: The Cleveland Clinic Foundation, Cleveland, OH (US)

(*) Notice: Subject to any disclaimer, the term of this patent is extended or adjusted under 35 U.S.C. 154(b) by 520 days.

(21) Appl. No.: 13/937,630

(22) Filed: Jul. 9, 2013

(65) Prior Publication Data
US 2014/0012260 A1    Jan. 9, 2014

Related U.S. Application Data

(60) Provisional application No. 61/669,188, filed on Jul. 9, 2012.

(51) Int. Cl.
*A61B 17/80* (2006.01)

(52) U.S. Cl.
CPC ........................ *A61B 17/80* (2013.01)

(58) Field of Classification Search
CPC .............................. A61B 17/809; A61B 17/80
USPC ........................................ 606/71, 105
See application file for complete search history.

(56) References Cited

U.S. PATENT DOCUMENTS

| | | | | |
|---|---|---|---|---|
| 2,406,832 A * | 9/1946 | Hardinge | ........... | A61B 17/8009 606/71 |
| 5,941,878 A | 8/1999 | Medoff | | |
| 6,402,756 B1 * | 6/2002 | Ralph | ................. | A61B 17/7059 606/287 |
| 8,048,077 B2 * | 11/2011 | Mor | ..................... | A61B 17/8076 606/280 |
| 8,343,190 B1 * | 1/2013 | Muelle | ................ | A61B 17/7068 606/248 |
| 8,475,504 B2 * | 7/2013 | Gillard | ................ | A61B 17/1684 606/281 |
| 2009/0281577 A1 | 11/2009 | Graham et al. | | |
| 2011/0106081 A1 | 5/2011 | Graham et al. | | |
| 2013/0096629 A1 * | 4/2013 | Rollinghoff | ........... | A61B 17/80 606/281 |

FOREIGN PATENT DOCUMENTS

WO    WO2012/003884    *    1/2012

* cited by examiner

*Primary Examiner* — David Bates
(74) *Attorney, Agent, or Firm* — Tarolli, Sundheim, Covell & Tummino LLP

(57) ABSTRACT

A bone fixation assembly to promote healing of a bone fracture comprises a first bone engagement member and a second bone engagement member. The first bone engagement member comprises an elongated body with proximal and distal end portions, a projection, and an inner surface defining an opening. The second bone engagement member comprises a main body, first and second outer surfaces, an inner surface defining an aperture, and an inner surface defining an opening spaced from the aperture. One of the end portions of first bone engagement member is dimensioned to extend through the aperture of the second bone engagement member. The opening of the first bone engagement member and the opening of the second bone engagement member are aligned to receive a fastener when the elongated body extends through the aperture and contacts an outer surface of the second bone engagement member.

10 Claims, 6 Drawing Sheets

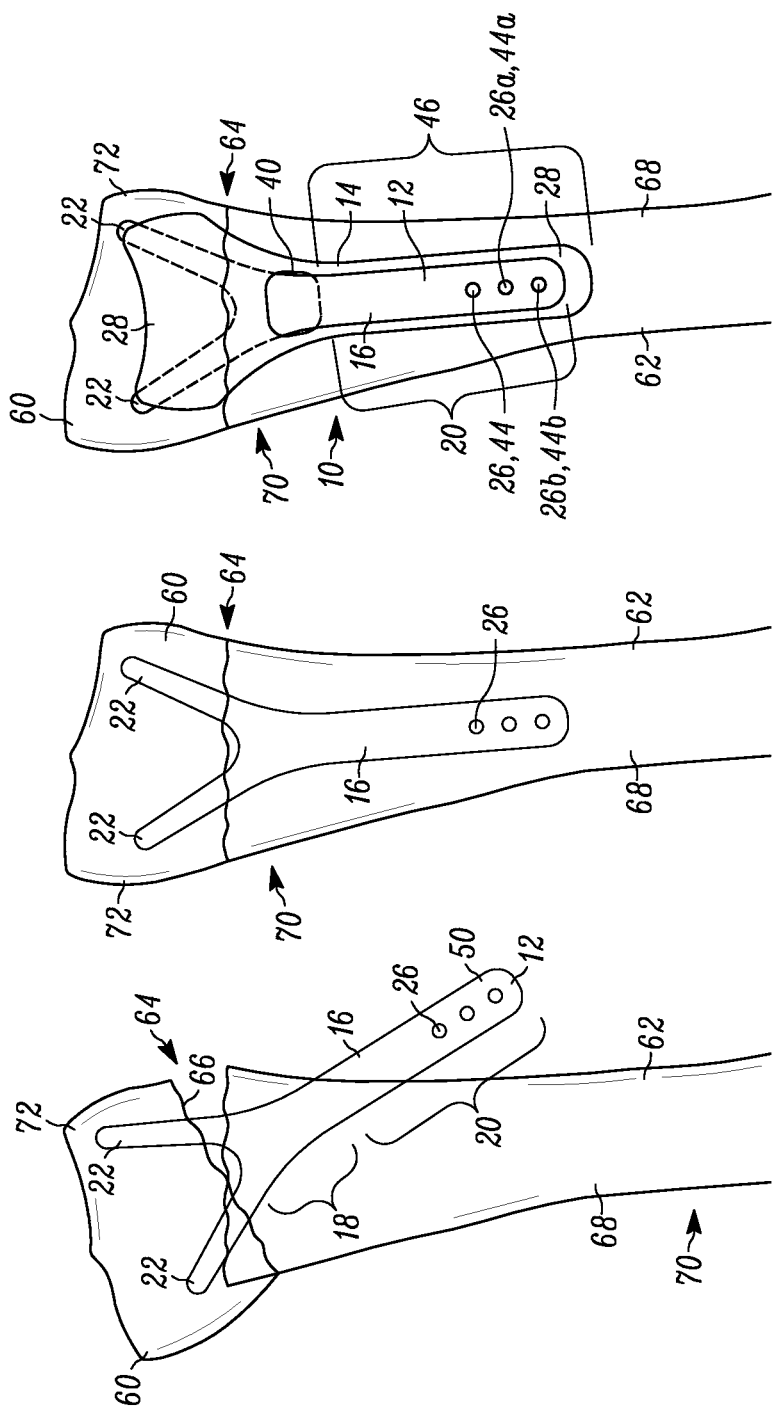

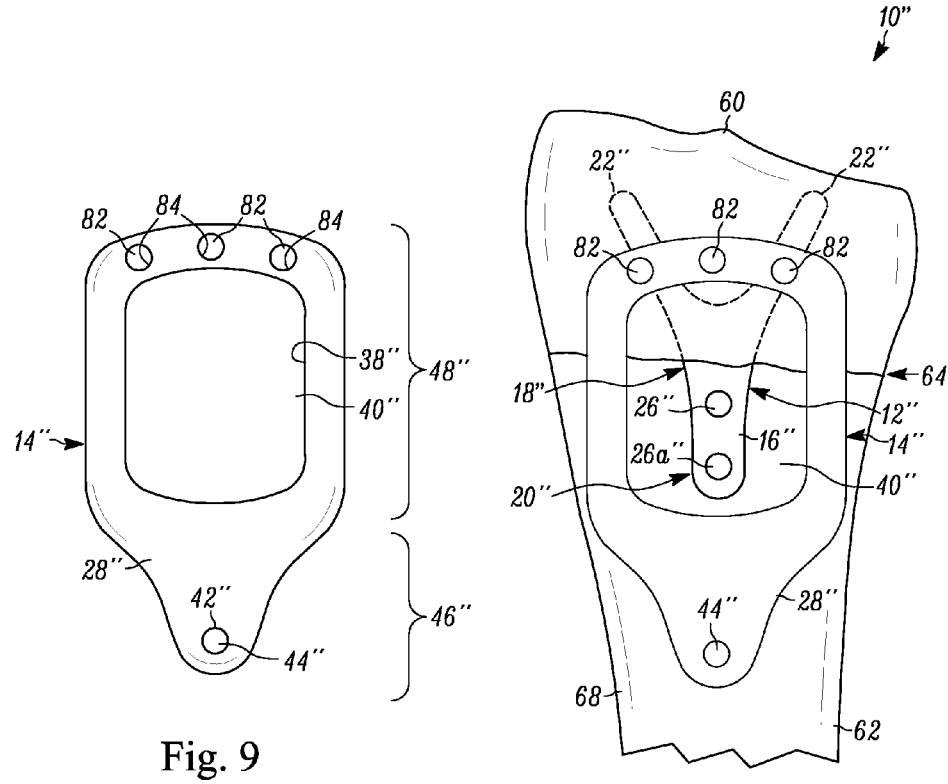
Fig. 9
Fig. 10
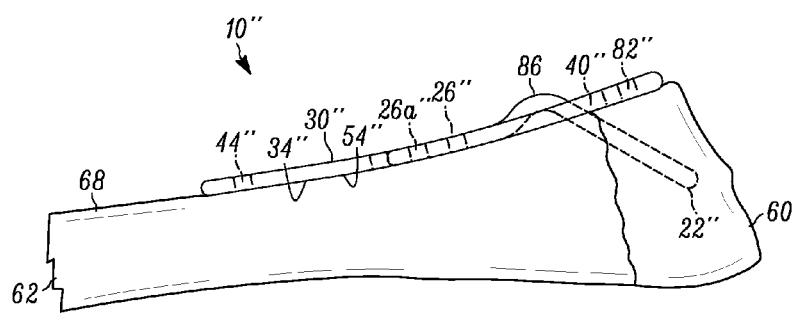
Fig. 11

BONE FIXATION ASSEMBLY

CROSS-REFERENCE TO RELATED APPLICATION

This application claims the benefit of U.S. Provisional Patent Application No. 61/669,188, filed Jul. 9, 2012 and entitled BONE FIXATION ASSEMBLY, which is incorporated herein by reference in its entirety.

TECHNICAL FIELD OF THE INVENTION

The present invention relates to an assembly to promote healing of a fracture between portions of bone tissue and, more particularly, to an assembly comprising two bone engagement members for reducing and stabilizing a bone fracture.

BACKGROUND OF THE INVENTION

Bone fixation assemblies are used to promote healing of a bone fracture by reducing the fracture and then stabilizing the pieces of the fractured bone. To help reduce the fracture, a first member of a bone fixation assembly is engaged with a bone piece and used to manipulate the bone piece into a desired position. A second member of the bone fixation assembly is engaged with a second bone piece, as well as with the first member of the assembly, to hold the bone pieces in position while the fracture heals.

SUMMARY OF THE INVENTION

The present invention is directed to an assembly to promote healing of a fracture between portions of bone tissue and, more particularly, to an assembly comprising two bone engagement members for reducing and stabilizing a bone fracture.

In accordance with an embodiment of the present invention, a bone fixation assembly comprises a first bone engagement member. The first bone engagement member includes an elongated body with a proximal end portion and a distal end portion. The elongated body includes a first inner surface defining an opening located in one of the proximal and distal end portions of the elongated body. A projection extends away from the elongated body. The bone fixation assembly also comprises a second bone engagement member. The second bone engagement member includes a main body. The main body includes a first outer surface presented in a first direction, and a second outer surface presented away from the first outer surface in a second direction. A second inner surface extends between the first and second outer surfaces. The second inner surface defines an aperture through the second bone engagement member. A third inner surface defines an opening spaced from the aperture. The one of the proximal and distal end portions of the elongated body of the first bone engagement member is dimensioned to extend through the aperture of the second bone engagement member. The opening located in the one of the proximal and distal end portions of the elongated body of the first bone engagement member and the opening in the second bone engagement member are aligned to receive a fastener when the one of the proximal and distal end portions of the elongated body of the first bone engagement member extends through the aperture of the second bone engagement member and the first bone engagement member contacts the first outer surface of the second bone engagement member.

In accordance with another embodiment of the present invention, a bone fixation assembly comprises a first bone engagement member. The first bone engagement member includes an elongated body with a proximal end portion and a distal end portion. The elongated body includes a first outer surface presented in a first direction and a second outer surface presented away from the first outer surface in a second direction. A projection extends away from the elongated body. The bone fixation assembly also includes a second bone engagement member. The second bone engagement member includes a main body. The main body includes a third outer surface presented in a third direction, and a fourth outer surface presented away from the third outer surface in a fourth direction. A first inner surface extends between the third and fourth outer surfaces. The first inner surface defines an aperture through the second bone engagement member. One of the proximal and distal end portions of the elongated body of the first bone engagement member is dimensioned to extend through the aperture of the second bone engagement member. The first outer surface of the first bone engagement member is configured to contact the fourth outer surface of the second bone engagement member when the one of the proximal and distal end portions of the elongated body of the first bone engagement member extends through the aperture of the second bone engagement member.

In accordance with a further embodiment of the present invention, a method of promoting healing of a bone fracture using a bone fixation assembly is provided. The bone fixation assembly comprises a first bone engagement member and a second bone engagement member. The first bone engagement member includes (a) an elongated body with a proximal end portion and a distal end portion, (b) a projection that extends away from the elongated body, and (c) a first inner surface defining an opening. The second bone engagement member includes a main body with a second inner surface that defines an aperture, and a third inner surface that defines an opening. The method comprises the step of engaging the projection of the first bone engagement member with an intramedullary portion of a first bone piece. The method also comprises the step of engaging the second bone engagement member with an extramedullary portion of a second bone piece. The method further comprises the step of extending one of the proximal and distal end portions of the first bone engagement member through the aperture of the second bone engagement member. The method still further comprises the step of aligning the opening in the first bone engagement member with the opening in the second bone engagement member and inserting a fastener through the aligned openings into the second bone piece.

BRIEF DESCRIPTION OF THE DRAWINGS

The foregoing and other features and advantages of the present invention will become apparent to one skilled in the art upon consideration of the following description of the invention and the accompanying drawings, in which:

FIG. 3A is a plan view of the first bone engagement member of FIG. 1A engaging an intramedullary portion of a first bone piece to facilitate reduction of a fracture;

FIG. 3B is a plan view of the first bone engagement member of FIG. 1A after having reduced the fracture of FIG. 3A;

FIG. 3C is a plan view of the first bone engagement member of FIG. 1A and the second bone engagement member of FIG. 2A arranged in an overlapping relationship over the reduced fracture of FIG. 3B;

FIG. 9 is a plan view of another modified second bone engagement member in accordance with the present invention;

FIG. 10 is a plan view of another modified first bone engagement member in use with the modified second bone engagement member of FIG. 9; and FIG. 11 is side view of the bone engagement members in use as shown in FIG. 10.

DETAILED DESCRIPTION OF THE INVENTION

Figure 1A:
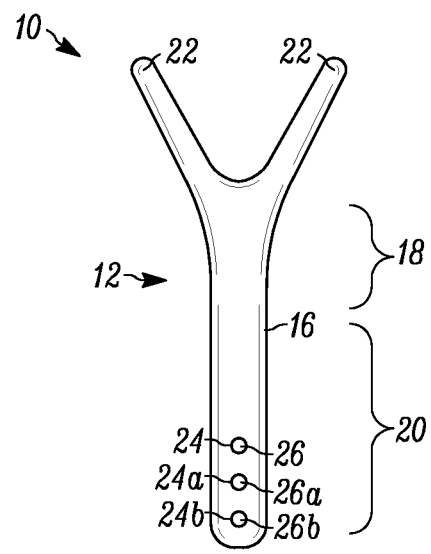
FIG. 1A is a plan view of a first bone engagement member, in accordance with the present invention.
Figure 1B:
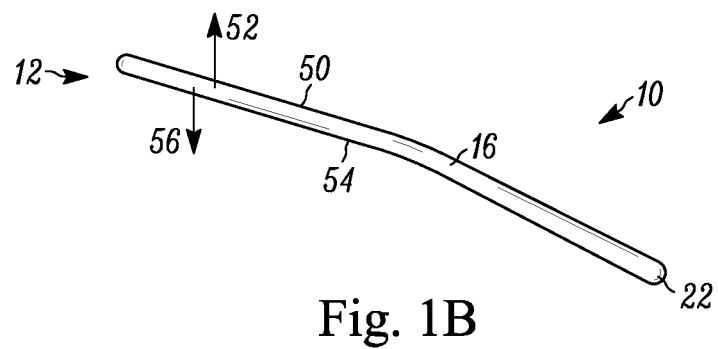
FIG. 1B is a side view of the first bone engagement member of FIG. 1A.
Figure 2A:
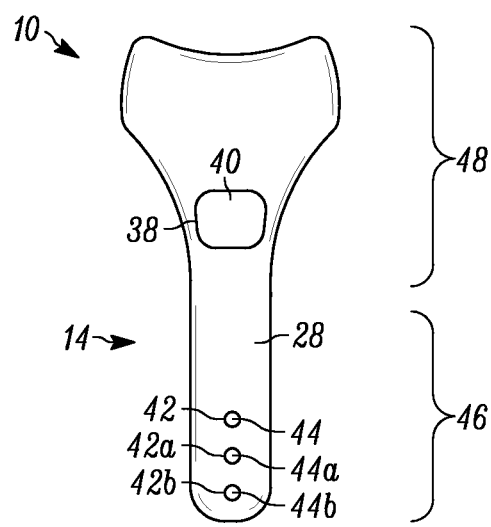
FIG. 2A is a plan view of a second bone engagement member, in accordance with the present invention.
Figure 2B:
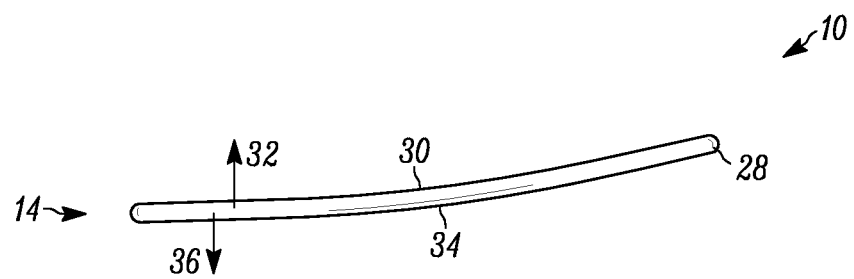
FIG. 2B is a side view of the second bone engagement member of FIG. 2A.

FIGS. 1A-2B show components of a bone fixation assembly 10 in accordance with an example of the present invention. The bone fixation assembly 10 comprises a first bone engagement member 12 (FIGS. 1A-1B) and a second bone engagement member 14 (FIGS. 2A-2B). The first bone engagement member 12 includes an elongated body 16. The elongated body 16 includes a first end portion 18 and a second end portion 20. As shown, the first end portion 18 is a proximal end portion of the elongated body 16, but the first end portion may alternatively be a distal end portion. Similarly, as shown, the second end portion 20 is a distal end portion of the elongated body 16, but the second end portion 20 may alternatively be a proximal end portion. The first bone engagement member 12 is made of a relatively rigid biocompatible material, such as medical grade stainless steel or titanium.

The first bone engagement member 12 is generally Y-shaped and includes two projections 22 that extend away from the elongated body 16. The first bone engagement member 12 may include more than two projections 22 or only one projection 22. As shown, the projections 22 extend away from the first end portion 18 of the elongated body 16, but may alternatively extend away from the second end portion 20 of the elongated body 16.

The elongated body 16 includes an upwardly-facing (as viewed in FIG. 1B) outer surface 50 presented in a direction 52. Opposite the outer surface 50 is a downwardly-facing (as viewed in FIG. 1B) outer surface 54 presented in a direction 56 opposite from the direction 52. The elongated body 16 also includes an inner surface 24 that defines an opening 26 in the elongated body 16. The inner surface 24 and the opening 26 extend from the outer surface 50 entirely through the elongated body 16 to the outer surface 54. The opening 26 is spaced away from the projections 22 and is configured and dimensioned to receive a fastener (not shown in FIGS. 1A and 1B), such as a bone screw. As shown, the projections 22 extend away from the first end portion 18 of the elongated body 16 and the opening 26 is located in the opposite, second end portion 20. The opening 26 may alternatively be located in the first end portion 18 of the elongated body 16, if the projections 22 extend away from the second end portion 20. The elongated body 16 also includes additional openings 26a-b defined by additional inner surfaces 24a-b. Such additional openings 26a-b are optional.

The second bone engagement member 14 (FIGS. 2A-2B) includes a main body 28. The main body 28 includes a first end portion 46 and a second end portion 48. An upwardly-facing (as viewed in FIG. 2B) outer surface 30 of the main body 28 is presented in a first direction 32. Opposite the outer surface 30 is a downwardly-facing (as viewed in FIG. 2B) outer surface 34 presented in a second direction 36 opposite from the first direction 32.

The main body 28 of the second bone engagement member 14 also includes an inner surface 38. The inner surface 38 extends entirely through the main body 28 from the outer surface 30 to the outer surface 34. The inner surface 38 defines an aperture 40 extending through the main body 28 of the second bone engagement member 14. As shown, the aperture 40 is located in the second end portion 48 of the main body 28. Alternatively, the aperture 40 may be located in the first end portion 46 of the main body 28. The aperture 40 is configured and dimensioned to receive the second end portion 20 of the elongated body 16 of the first bone engagement member 12. The second end portion 20 is correspondingly configured and dimensioned to extend through the aperture 40 of the main body 28 of the second bone engagement member 14.

Another inner surface 42 extends entirely through the main body 28 of the second bone engagement member 14 from the outer surface 30 to the outer surface 34. The inner surface 42 defines an opening 44. The opening 44 is located in the first end portion 46 of the main body 28 of the second bone engagement member 14. The opening 44 is spaced away from the aperture 40 and is configured and dimensioned to receive a fastener (not shown in FIGS. 2A and 2B), such as a bone screw. The main body 28 also includes additional openings 44a-b defined by additional inner surfaces 42a-b located in the first end portion 46 of the main body 28. Such additional openings 44a-b are optional. The number of additional openings 44a-b is the same as the number of additional openings 26a-b located in the elongated body 16 of the first bone engagement member 12.

To assemble the bone fixation assembly 10, the first bone engagement member 12 and the second bone engagement member 14 are engaged with each other. In particular, the first bone engagement member 12 is positioned below the second bone engagement member 14. The second end portion 20 of the elongated body 16 of the first bone engagement member 12 is inserted into the aperture 40 of the main body 28 of the second bone engagement member 14. After the second end portion 20 of the elongated body 16 has been inserted into the aperture 40, the second end portion of the elongated body is pivoted or otherwise moved toward the first end portion 46 of the main body 28 of the second bone engagement member 14. The downwardly-facing outer surface 54 of the elongated body 16 is thereby moved toward and into contact with the upwardly-facing outer surface 30 of the main body 28. The downwardly-facing outer surface 54 of the elongated body 16 of the first bone engagement member 12 thus contacts the upwardly-facing outer surface 30 of the main body 28 of the second bone engagement member 14 when the second end portion 20 of the elongated body extends through the aperture 40 of the second bone engagement member. The main body 28 and the elongated body 16 are disposed in generally parallel planes when the outer surface 54 contacts the outer surface 30.

After the elongated body 16 of the first bone engagement member 12 is passed through the aperture 40 of the main body 28 of the second bone engagement member 14 and the outer surface 54 of the elongated body 16 contacts the outer surface 30 of the main body 28, the first bone engagement member and the second bone engagement member are arranged in a desired final position. In the desired final position, the opening 26 located in the elongated body 16 of the first bone engagement member 12 and the opening 44 located in the main body 28 of the second bone engagement member 14 are aligned to receive a fastener (not shown). The outer surface 54 of the elongated body 16 of the first bone engagement member 12 thus contacts the outer surface 30 of the main body 28 of the second bone engagement member 14 so that the openings 26, 44 are generally aligned. The elongated body 16 can be further positioned such that the openings 26, 44 and the additional openings 26a-b, 44a-b are substantially aligned. The main body 28 and the elongated body 16 are disposed in generally parallel planes when the downwardly-facing outer surface 54 contacts the upwardly-facing outer surface 30.

Figure 4:
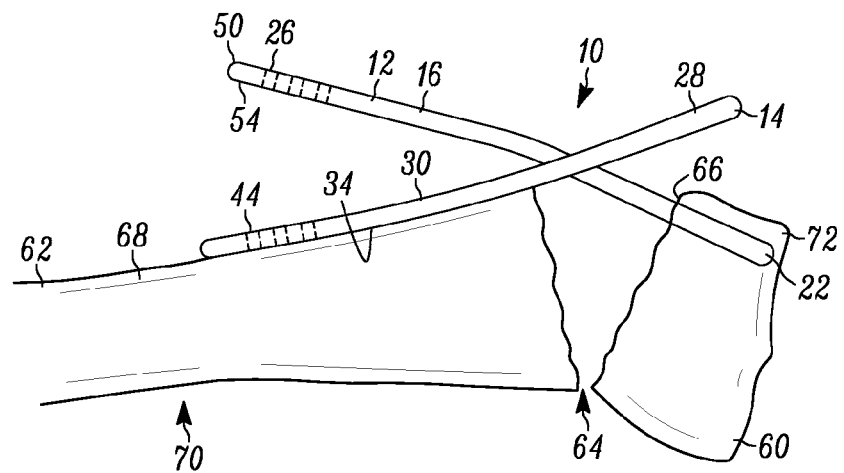
FIG. 4 is a side view of the first bone engagement member of FIG. 1A extending through an aperture in the second bone engagement member of FIG. 2A.
Figure 5:
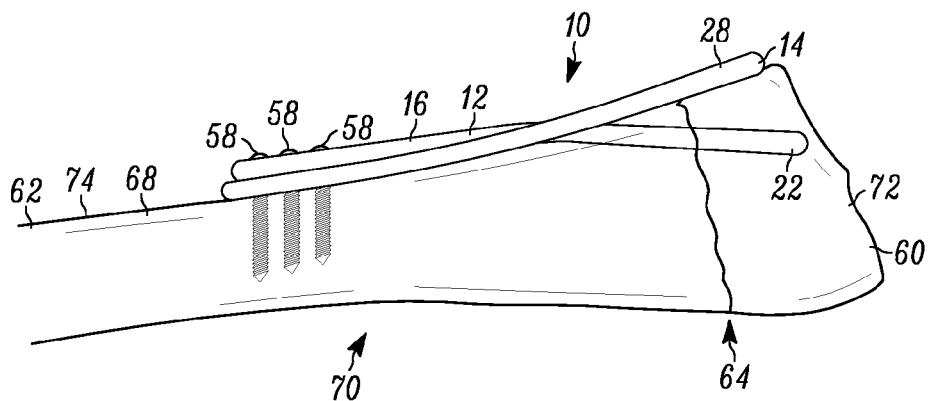
FIG. 5 is a side view of the first bone engagement member of FIG. 1A and the second bone engagement member of FIG. 2A fixed to bone pieces.

In use, as shown in FIGS. 4-5, the first bone engagement member 12 and the second bone engagement member 14 engage pieces 60, 62 of a fractured bone 70 to promote healing of the bone fracture 64. The projections 22 of the first bone engagement member 12 engage an intramedullary portion 66 of the first bone piece 60. This engagement facilitates manipulation of the first bone piece 60 using the first bone engagement member 12 to reduce the fracture 64. The second bone engagement member 14 is arranged so that the downwardly-facing outer surface 34 of the main body 28 of the second bone engagement member contacts an extramedullary portion 68 of the second bone piece 62. The outer surface 34 of the main body 28 may also contact the extramedullary portion 72 of the first bone piece 60, as shown in FIG. 5.

FIGS. 3A-5 illustrate a method of using the above described bone fixation assembly 10 to promote healing of the fracture 64 in the bone 70 by reducing the fracture and stabilizing the first and second bone pieces 60, 62 while the fractured bone heals.

The first step in the method is to install the first bone engagement member 12. Specifically, as shown in FIG. 3A, the projections 22 of the first bone engagement member 12 are engaged with the intramedullary portion 66 of the first piece 60 of the bone 70.

After the first bone engagement member 12 is installed in the first bone piece 60, the next step in the method is to move the first bone piece 60 into its natural or normal position with respect to the second bone piece 62. The first bone piece 60 is moved via a force applied to the elongated body 16 of the first bone engagement member 12. As force is applied to the elongated body 16, the first bone piece 60 is rotated about an axis or otherwise moved toward the second bone piece 62 and into its natural or normal position with respect to the second bone piece. FIG. 3B shows the first bone piece 60 having been manipulated into its natural position with respect to the second bone piece 62 using the first bone engagement member 12.

After the first bone piece 60 is properly positioned with respect to the second bone piece 62 using the first bone engagement member 12, the next step in the method is to insert the second end portion 20 of the elongated body 16 of the first bone engagement member 12 into the aperture 40 of the main body 28 of the second bone engagement member 14, as shown in FIG. 3C. The second bone engagement member 14 is then, in a further step of the method, positioned with respect to the second bone piece 62 such that the surface 34 of the main body 28 contacts the extramedullary portion 68 of the second bone piece.

After the elongated body 16 is extended through the aperture 40 and the second bone piece 62 is positioned such that the surface 34 of the main body 28 contacts the extramedullary portion 68 of the second bone piece, the method proceeds to a step of moving the elongated body toward the first end portion 46 of the second bone engagement member 14. When the elongated body 16 is properly positioned, the downwardly-facing outer surface 54 of the elongated body is disposed on top of the upwardly-facing outer surface 30 of the main body 28 such that the elongated body 16 and the main body 28 are disposed in generally parallel planes.

The next step in the method is to align the openings 26, 26a, 26b of the elongated body 16 and the openings 44, 44a, 44b of the main body 28. Once the outer surface 54 of the elongated body 16 is disposed on top of the outer surface 30 of the main body 28, the openings 26, 26a, 26b and the openings 44, 44a, 44b may be generally aligned. The elongated body 16 is then further positioned, as may be required, with respect to the main body 28 so that the openings 26, 26a, 26b and the openings 44, 44a, 44b are substantially aligned.

As the final step in the method, fasteners 58 are inserted through the now-aligned openings 26, 26a, 26b of the elongated body 16 and openings 44, 44a, 44b of the main body 28. The fasteners 58 pass through an outer surface 74 of the extramedullary portion 68 of the second bone piece 62. The fasteners 58 secure both the first bone engagement member 12 and the second bone engagement member to the second bone piece 62. FIG. 5 shows the fully installed bone fixation assembly 10.

Although the foregoing description presents installing the first bone engagement member 12 in the first bone piece 60, moving the first bone piece, extending the elongated body 16 through the aperture 40, contacting the extramedullary portion 68 of the second bone piece 62 with the surface 34 of the main body 28, and moving the elongated body toward the second end portion 46 of the second bone engagement member as five discrete and sequential steps in the method, certain of the steps may be performed in a different order and/or two or more of the steps may be performed together. For example, in appropriate circumstances, the second bone engagement member 14 may be positioned in contact with the second bone piece 62 before the first bone engagement member 12 is installed in the first bone piece 60. In such circumstances, the step of moving the first bone piece 60 to reduce the fracture 64 and the step of extending the elongated body 16 through the aperture 40 in the second bone engagement member 14 may be performed simultaneously.

Figure 6:
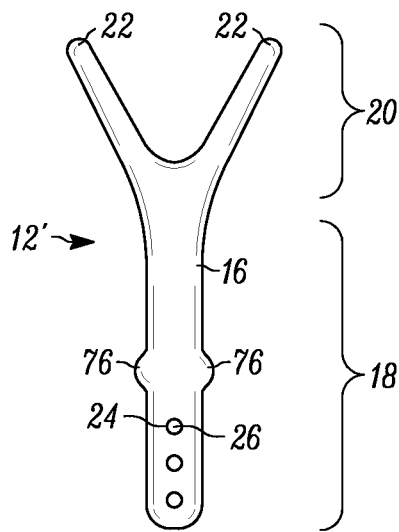
FIG. 6 is a plan view of a modified first bone engagement member in accordance with the present invention.

FIG. 6 shows a modified version of the first bone engagement member 12, in accordance with the present invention. The modified first bone engagement member 12' includes all of the same elements found in the first bone engagement member 12 of FIGS. 1-5. The modified first bone engagement member 12' also includes two tabs 76 located on the elongated body 16 between the opening 26 and the projections 22. The tabs 76 project laterally away from one another on opposite edges of the elongated body 16. The tabs 76 are configured to contact the outer surface 30 of the main body 28 of the second bone engagement member 14.

Figure 7:
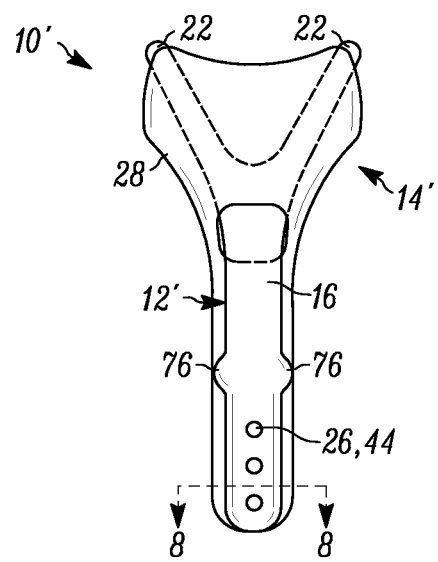
FIG. 7 is a plan view of the modified first bone engagement member of FIG. 6 engaging a modified second bone engagement member.

FIG. 7 shows the modified first bone engagement member 12' engaged with a modified second bone engagement member 14' to form a modified bone fixation assembly 10'. The modified second bone engagement member 14' includes all of the same elements found in the second bone engagement member 14 of FIGS. 1-5. The main body 28 also includes indentations (not shown) to receive the tabs 76 to help position the modified first bone engagement member 12' with respect to the modified second bone engagement member 14' so that the openings 26, 44 are substantially aligned. The tabs 76 contact the upwardly-facing outer surface 30 of the main body 28. The tabs 76 may snap into the indentations (not shown) in main body 28. The tabs 76 of the modified first bone engagement member 12' help to align the opening 26 of the elongated body 16 with the opening 44 of the main body 28 of the modified second bone engagement member 14'.

Figure 8:
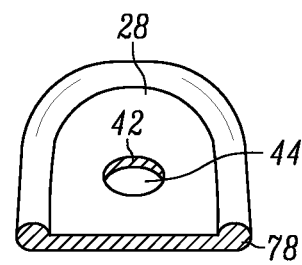
FIG. 8 is an enlarged sectional view of a portion of the modified second bone engagement member taken along line 8-8 of FIG. 7.

FIG. 8 shows a sectional view of a portion of the modified second bone engagement member 14'. The main body 28 of the modified second bone engagement member 14' includes a thickened peripheral edge or raised lip 78 to help keep the modified first bone engagement member 12' and the modified second bone engagement member 14' in proper alignment. The modified first bone engagement member 12' is dimensioned to fit within the area enclosed by the lip 78. The lip 78 thus helps to prevent the modified first bone engagement member 12' from shifting laterally with respect to the modified second bone engagement member 14' after the modified first and second bone engagement members have been positioned in proper alignment.

FIG. 9 shows another modified version of the second bone engagement member 14, in accordance with the present invention. The modified second bone engagement member 14" of FIG. 9 includes the same elements found in the second bone engagement member 14 of FIGS. 2-5, except for the additional openings 44a-b in the first end portion 46 of the main body 28. The elements of the modified second bone engagement member 14" are identified with the same reference numerals as the elements of the second bone engagement member 14 of FIGS. 2-5 with the addition of a double prime ("). As can be seen by comparing FIG. 9 with FIG. 2A, the aperture 40" that extends through the main body 28" of the modified second bone engagement member 14" is larger in proportion to the main body 28" than the aperture 40 is in proportion to the main body 28 of the second bone engagement member 14. In addition, the modified second bone engagement member 14" includes a plurality of openings 82 in second end portion 48" of the modified second bone engagement member. Each opening 82 is defined by a surface 84 that extends entirely through the main body 28" from the outer surface 30" to the outer surface 34". The openings 82 are positioned in the second end portion 48" such that the aperture 40" is disposed between the openings 82 and the opening 44" in the first end portion 46" of the modified second bone engagement member 14".

The modified second bone engagement member 14" of FIG. 9 can be used with the first bone engagement member 12 of FIGS. 1A-B. The modified second bone engagement member 14" can also be used with a modified first bone engagement member 12", as shown in FIGS. 10 and 11. The modified first bone engagement member 12" shown in FIGS. 10 and 11 includes the same elements found in the first bone engagement member 12 of FIGS. 1A-B, except that the modified first bone engagement member only includes a single additional opening 26a" in the second end portion 20" of the elongated body 16". The elements of the modified first bone engagement member 12" are identified with the same reference numerals as the elements of the first bone engagement member 12 of FIGS. 1A-B with the addition of a double prime ("). As can be seen by comparing FIG. 10 with FIG. 1A, the elongated body 16" of the modified first bone engagement member 12" is shorter than the elongated body 16 of the first bone engagement member 12. In addition, the elongated body 16" includes a slightly upwardly curved arc or hump 86 in its first end portion 18", as viewed in FIG. 11. Beyond the hump 86, the projections 22" of the modified first bone engagement member 12" extend both away from the elongated body 16" and downwardly from the elongated body 16", as viewed in FIG. 11.

When the modified first bone engagement member 12" is used with the modified second bone engagement member 14" to form a modified bone fixation assembly 10", the shorter elongated body 16" of the modified first bone engagement member can fit entirely within the larger aperture 40" of the modified second bone engagement member, as can be seen in FIGS. 10 and 11. Specifically, the elongated body 16" and the aperture 40" are configured and dimensioned to permit the elongated body 16" to fit entirely with the aperture 40". Accordingly, when the modified first bone engagement member 12" is used to manipulate the first bone piece 60 of the bone 70 into its normal or otherwise desired position relative to the second bone piece 62, the downwardly facing outer surface 54" of the elongate body 16" can contact the extramedullary portion 68 of the second bone piece 62, as shown in FIG. 11. The modified second bone engaging member 14" is then secured to both the first bone piece 60 and the second bone piece 62 by inserting fasteners (not shown) through the openings 82 and the opening 44", respectively. With the fasteners (not shown) engaging the modified second bone engagement member 14" and the first and second bone pieces 60 and 62, the modified second bone engagement member helps to stabilize the bone pieces. The modified first bone engagement member 12" may then either be removed entirely from the bone 70 or be secured to the second bone piece 62 by inserting fasteners (not shown) through the openings 26" and 26a".

Although the first bone engagement member 12 and the modified first bone engagement members 12', 12" are generally Y-shaped and include two projections 22, 22" that extend away from the elongated body 16, 16", the number of projections 22, 22" may be smaller or greater than two, and the overall shape of the first bone engagement member and the modified first bone engagement members may vary accordingly. Similarly, the length of the projections 22, 22" may be greater or less than the lengths shown in the Figures, and the angles at which the projections extend, both laterally and vertically, away from the elongated bodies 16, 16" may vary from the angles shown in the Figures. In addition, while the elongated body 16" of the modified first bone engagement member 12" can fit entirely within the aperture 40" of the modified second bone engagement member 14", the elongated body may have a length sufficient to permit one of the opening 26, 26a to be aligned with the opening 44" in the modified second bone engagement member 14" so as to be able to receive a fastener through the aligned openings.

From the above description of the invention, those skilled in the art will perceive improvements, changes, and modifications. Such improvements, changes, and/or modifications within the skill of the art are intended to be covered by the appended claims.

Having described the invention, the following is claimed:

1. A bone fixation assembly comprising:
   a first bone engagement member including:
   an elongated body with a proximal end portion and a distal end portion, the elongated body including a first inner surface defining an opening located in a selected one of the proximal and distal end portions of the elongated body, and
   a projection extending away from the elongated body; and a second bone engagement member including:
  a main body, the main body including:
    a first outer surface presented in a first direction,
    a second outer surface presented away from the first outer surface in a second direction,
    a second inner surface extending between the first and second outer surfaces, the second inner surface defining an aperture extending through the first and second outer surfaces of the second bone engagement member, and
    a third inner surface defining an opening axially spaced from the aperture along a long axis of the second bone engagement member;
  the selected one of the proximal and distal end portions of the elongated body of the first bone engagement member being dimensioned to extend through the aperture of the second bone engagement member, and
  the opening located in the selected one of the proximal and distal end portions of the elongated body and the opening of the second bone engagement member being aligned to receive a fastener through the opening of the second bone engagement member and the opening of the elongated body when the selected one of the proximal and distal end portions of the elongated body of the first bone engagement member extends through the aperture of the second bone engagement member and the first bone engagement member contacts the first outer surface of the second bone engagement member.

2. The bone fixation assembly of claim 1, wherein the first bone engagement member includes a third outer surface presented in a third direction and a fourth outer surface presented away from the third outer surface in a fourth direction, the fourth outer surface of the first bone engagement member being configured to contact the first outer surface of the second bone engagement member when the selected one of the proximal and distal end portions of the elongated body of the first bone engagement member extends through the aperture of the second bone engagement member.

3. The bone fixation assembly of claim 2, wherein the fourth outer surface of the first bone engagement member contacts the first outer surface of the second bone engagement member when the opening located in the selected one of the proximal and distal end portions of the elongated body of the first bone engagement member and the opening of the second bone engagement member are aligned.

4. The bone fixation assembly of claim 1, wherein the projection of the first bone engagement member is configured to engage an intramedullary portion of a first bone piece.

5. The bone fixation assembly of claim 1, wherein the first bone engagement member is configured to contact the first outer surface of the second bone engagement member so that the main body of the second bone engagement member and the elongated body of the first bone engagement member are disposed in generally parallel planes.

6. The bone fixation assembly of claim 1, wherein the second bone engagement member is configured to contact an extramedullary portion of a first bone piece, an extramedullary portion of a second bone piece, and an outer surface of the first bone engagement member.

7. The bone fixation assembly of claim 1, wherein the second outer surface of the second bone engagement member is configured to contact the extramedullary portion of at least one of a first and second bone pieces.

8. The bone fixation assembly of claim 1, wherein the main body of the second bone engagement member and the elongated body of the first bone engagement member are disposed in generally parallel planes when the selected one of the proximal and distal end portions of the elongated body of the first bone engagement member extends through the aperture of the second bone engagement member and the first bone engagement member contacts the first outer surface of the second bone engagement member.

9. The bone fixation assembly of claim 1, wherein the first bone engagement member includes a plurality of projections that extend away from the elongated body.

10. A bone fixation assembly comprising:
  a first bone engagement member including:
    an elongated body with a proximal end portion and a distal end portion, the elongated body including a first outer surface presented in a first direction and a second outer surface presented away from the first outer surface in a second direction, and
    a projection extending away from the elongated body; and
    the elongated body including an opening spaced apart from the projection; and
  a second bone engagement member including:
    a main body, the main body including:
      a third outer surface presented in a third direction,
      a fourth outer surface presented away from the third outer surface in a fourth direction, and
      a first inner surface extending between the third and fourth outer surfaces, the first inner surface defining an aperture through the third outer surface and the fourth outer surface of the second bone engagement member;
    a selected one of the proximal and distal end portions of the elongated body of the first bone engagement member being dimensioned to extend through the aperture of the second bone engagement member, and
    the first outer surface of the first bone engagement member being configured to contact the fourth outer surface of the second bone engagement member;
    with the opening being located directly adjacent the fourth outer surface of the second bone engagement member and being axially spaced a distance from the aperture along a long axis of the bone engagement member, the opening configured to receive a fastener therethrough, when the selected one of the proximal and distal end portions of the elongated body of the first bone engagement member extends through the aperture of the second bone engagement member.

* * * * *